(12) United States Patent
Egan et al.

(10) Patent No.: US 8,471,712 B2
(45) Date of Patent: Jun. 25, 2013

(54) DETECTING ABNORMAL TIME INTERVALS (75) Inventors: Blaise F. Egan, Chelmsford (GB);
Andrew A. Reeves, Ipswich (GB)

(73) Assignee: British Telecommunications public limited company, London (GB)

( * ) Notice: Subject to any disclaimer, the term of this patent is extended or adjusted under 35 U.S.C. 154(b) by 728 days.

(21) Appl. No.: 12/531,940

(22) PCT Filed: Mar. 7, 2008

(86) PCT No.: PCT/GB2008/000780
§ 371 (c)(1),
(2), (4) Date: Apr. 28, 2010

(87) PCT Pub. No.: WO2008/113971
PCT Pub. Date: Sep. 25, 2008

(65) Prior Publication Data
US 2010/0214103 A1    Aug. 26, 2010

(30) Foreign Application Priority Data
Mar. 20, 2007 (EP) ................... 07251160
Aug. 23, 2007 (EP) ................... 07253336

(51) Int. Cl.
*G08B 23/00* (2006.01)
(52) U.S. Cl.
USPC ................... 340/573.1; 340/573.4
(58) Field of Classification Search
USPC ......... 340/573.1, 506, 573.4, 539.14, 539.22; 379/38, 39
See application file for complete search history.

(56) References Cited

U.S. PATENT DOCUMENTS

| | | | |
|---|---|---|---|
| 5,058,599 A | | 10/1991 | Andersen |
| 5,692,215 A | * | 11/1997 | Kutzik et al. ............... 340/573.4 |
| 7,091,865 B2 | * | 8/2006 | Cuddihy et al. ........... 340/573.1 |
| 7,855,650 B2 | * | 12/2010 | Duckert et al. ............ 340/573.1 |
| 8,098,156 B2 | * | 1/2012 | Caler et al. ..................... 340/541 |
| 2005/0181771 A1 | | 8/2005 | Cuddihy et al. | |

FOREIGN PATENT DOCUMENTS

| | | |
|---|---|---|
| EP | 0 402 508 | 12/1990 |
| EP | 1 571 583 | 9/2005 |

OTHER PUBLICATIONS

International Search Report for PCT/GB2008/000780, mailed Apr. 10, 2008.

* cited by examiner

*Primary Examiner* — John A Tweel, Jr.
(74) *Attorney, Agent, or Firm* — Nixon & Vanderhye P.C.

(57) ABSTRACT

A system for determining if a time period after a sensing node has sensed an event exceeds a threshold value, including establishing means for establishing a plurality of reference threshold values, wherein each reference threshold value is associated with a set of reference inter-event time intervals or metrics statistically derived therefrom, calculating means for calculating a set of preliminary time intervals or metrics statistically derived therefrom, based on events sensed by the sensing node, comparing means for comparing the set of preliminary inter-event time intervals or metrics statistically derived therefrom, with each set of reference inter-event time intervals or metrics statistically derived therefrom, identifying means for identifying the reference threshold value associated with the set of reference inter-event time intervals or metrics statistically derived therefrom, being the closest match to the set of preliminary inter-event time intervals or metrics statistically derived therefrom, and determining means for determining if, upon the sensing node sensing a further event, the time period after the sensing node has sensed the event exceeds the identified reference threshold value before a yet further event is sensed by the sensing node or an associated sensing node.

12 Claims, 5 Drawing Sheets

PRIOR ART

DETECTING ABNORMAL TIME INTERVALS

This application is the U.S. national phase of International Application No. PCT/GB2008/000780 filed 7 Mar. 2008, which designated the U.S. and claims priority to European Application No(s). 07251160.3, filed 20 Mar. 2007 and 072533363, filed 23 Aug. 2007, the entire contents of each of which are hereby incorporated by reference.

BACKGROUND AND SUMMARY

This invention relates to apparatus, systems and methods for the detection of abnormal time intervals between events, in particular within the context of the remote monitoring of the wellbeing of persons.

"Telecare" is a term describing the use of technology to enable parties such as care providers to monitor the status of persons who may be elderly or otherwise vulnerable (referred herein as customers), where such customers remain in their own homes or are otherwise located remote to the care providers.

Various telecare approaches are known. In the most direct method of obtaining customer data, customers wear devices which measure certain physical or physiological parameters. For example, an accelerometer-based equipment worn on the person can provide direct feedback to the care provider that the customer has fallen. However this method suffers from being excessively invasive to the customer who may have to have on his person a number of such devices. Compliance is also a problem where the customer is reluctant to cooperate by wearing the device(s) especially if interaction with a complex user interface is required.

A preferred approach is to provide sensors fixed within the customer's premises, to monitor the customer's activities. This can be achieved by use of devices to literally keep an eye on the customer, such as video cameras and sound recording devices. However this approach could also be ethically objectionable and invasive; it is also expensive and complicated to set up and monitor.

A third and still less invasive approach is to capture data indirectly about the customer's movements and actions. Such data is obtained by use of ambient sensors such as passive infrared (PIR) motion sensors, sensors to detect door and window closure, meters to detect use of water, electric and gas, and the like. These devices can continually capture information about the activity and inactivity levels and patterns of the customer with greater subtlety than by use of wearable devices or by video cameras. As being technologically and commercially mature technologies, such sensors are relatively reliable and inexpensive to obtain, install (especially if they are wireless) and use. Sensed atypical inactivity, in particular, can be mapped to and signify an abnormal event (e.g. when the customer's behaviour deviates from the normal behaviour levels or pattern), such as a fall. The sensed data can then be fed into a monitoring system which analyses the data to determine the likelihood of an abnormal event existing, whereupon an alarm can be raised to the remote care providers. In this description, the term "event", depending on context, includes the occurrence of an event (sometimes "positive event") as well as the time interval between positive events, or the absence of events (a "negative event" or "non-event").

The present invention has application in any telecare system using any approach i.e. regardless of how the data is obtained, although the description herein will in the main refer to an embodiment and application in the context of system based on the use of motion sensors, door and window opening and closing sensors, bed occupancy, toilet usage, utility use meters and the like.

In such a system, the gathered information is analysed to determine if a pre-determined condition is met. As an example, periods of non-movement can be identified by motion sensors so that a period of non-movement exceeding a pre-determined length of time is deemed to be unusual, and indicative that the customer has fallen.

In the present description, an "inter-event" time period is the length of time elapsed between consecutive positive events detected by either the same sensor or all sensors within the dwelling of a particular customer. Put another way, an "inter-event" period is the duration of a negative event. In a telecare system, a threshold value defines the boundary of an acceptable inter-event period. If the sensor, or group of sensors, fails to detect an event beyond a set threshold value, this may be deemed to be an abnormal occurrence deserving attention. Thus, the term "inter-event time interval" could also in an appropriate context refer to a time interval following the end of a positive event where there may be a late or even no following positive event, especially in the context of discovering if any positive event ending this time period occurs soon enough to be acceptable.

The main problem for the telecare system operator is in deciding where to set the threshold value of the non-movement period. If the value is set too low, then an excessive number of false alarms will be generated, annoying all concerned and more significantly, reducing trust in the system. Setting the threshold level too high however, carries the risk of an alarm being raised late which means that assistance would be sent late to the customer needing help.

There are currently two main approaches to the determination of the threshold value. In the first, a fixed value is provided at the outset. This is currently the prevalent method deployed by telecare operators, where sensors (also here referred to as nodes) have their threshold values either factory-set, or set by the parties installing the sensors at the premises or dwellings. The threshold value is thus often at best an educated guess about its applicability or accuracy in the particular implementation. Even where the value can be subsequently changed, this is a clumsy method requiring much separate measurement and monitoring before the value can be manually re-set.

"Case Studies from the Liverpool Telecare Pilot" Barnes N, Webster S, Mizutani T, Reeves A, Ng J, Buckland M describes an adaptive approach which can be personalised to the customer through the system's "learning" the customer's behaviour and habits over time. The learning process is based on data gathered by a system of individual sensors or nodes within the customer's home and a gateway device to which all the nodes are connected. The threshold levels initially used are either factory-set, or else are set by the installers. As the sensor nodes gather data over time, it or the gateway device builds a statistical profile of the normal activity levels and behavioural patterns of the particular customer and uses this profile as the basis for predicting future behaviour. A problem arises however with the setting of the threshold value in this scenario. The applicant's experience in this field is that it can take weeks (in an optimistic scenario) or even months for accurate and reliable threshold values to be established. Indeed, in some cases it has been found that a reliable threshold value cannot be set even after 2.5 years. Until then, the system is still "learning" and while capable of sensing positive events, there is no threshold value to refer to. Unless and until a threshold value is sent, it is incapable of full operation to sense the occurrence of an abnormal event so as to generate alerts in a trusted manner in the event of customer difficulties.

The length of time needed for a telecare system to complete the "learning" or "training" phase and to establish threshold values is a problem and a significant barrier to the commercialisation and mass take-up of telecare systems.

There is thus a need for a system capable of becoming fully operational by establishing and setting threshold values within a shorter space of time. The present invention seeks to address this issue.

In a first aspect of the invention, there is provided a system for determining if a time period after a sensing node has sensed an event exceeds a threshold value, including establishing means for establishing a plurality of reference threshold values, wherein each reference threshold value is associated with a set of reference inter-event time intervals or metrics statistically derived therefrom, calculating means for calculating a set of preliminary time intervals or metrics statistically derived therefrom, based on events sensed by the sensing node, comparing means for comparing the set of preliminary inter-event time intervals or metrics statistically derived therefrom, with each set of reference inter-event time intervals or metrics statistically derived therefrom, identifying means for identifying the reference threshold value associated with the set of reference inter-event time intervals or metrics statistically derived therefrom, being the closest match to the set of preliminary inter-event time intervals or metrics statistically derived therefrom, and determining means for determining if, upon the sensing node sensing a further event, the time period after the sensing node has sensed the event exceeds the identified reference threshold value before a yet further event is sensed by the sensing node or an associated sensing node.

In the invention, a sensor or a node which is newly-installed in a dwelling can refer to a threshold value which has already been established and stored for the use of the new node. In this way, the "learning period" of the new node to establish its own threshold value is either eliminated or considerably reduced. The threshold level represents the boundary of a normal time interval between sensed events—failure to sense an event within the normal time period or interval has expired indicates an abnormal event to be investigated and may be cause to raise an alarm.

The stored threshold value can be one which has been pre-determined e.g. by the system administrator from experience or historical data, or one which is established by an "established" node already in use. In a preferred embodiment however, there are a number of stored threshold values generated by a number of established nodes. In this case, the new node can select from the number of reference threshold values, where each threshold value is associated with either a particular node, or cluster of nodes, or more preferably, with a set of metrics statistically derived from data about events sensed by the established or reference nodes, each metric in the set being such as to have caused a respective threshold value, equal or close to the respective reference value, to have been selected either manually or automatically for the respective established or reference node. The new node selects the node by first sensing a few events of its own after installation. These sensed events are compared with the sensed data obtained by the established node(s) for a match. Alternatively and more preferably, instead of comparing raw data with raw data, the raw data sensed by the nodes is processed using statistical methods (e.g. Standard Deviation) to produce metrics which are then used for comparison purposes.

The established node whose sensed data (which reference shall, where appropriate include metrics statistically derived from the sensed data), most closely matches the new node's own sensed data is selected, and the threshold value associated with that established node set for the new node.

It can be seen that the node types need not be the same for the application of this invention, i.e. if sensed data from a PIR sensor matches the sensed data from a gas metering device (e.g. there is a sensed event indicating activity or use every two hours)—the threshold value for the PIR sensor could well be applied for the gas meter. However it may be expected that sensed data between nodes sensing similar types of data are more likely to produce threshold values which are useful to newly-established which are similarly set up to sense similar types of data.

The sensed data is preferably described in statistical terms, especially by reference to the mean and standard deviation of the gathered data. The matching method can be carried out using any conventional technique: if the data is described statistically then it is sensible to use statistical methods to analyse the data to find a match e.g. by using a case based reasoning engine.

In a further preferred embodiment, a number of threshold values are established for the node. These threshold values could correspond to time of day periods where each period comprises e.g. two hours. For example, it may be expected that a sensor node in the kitchen may more frequently detect activity during meal times than during the midnight hours. Thus different threshold levels will be set for the hours of 18:00 to 20:00, as compared to 02:00 to 04:00.

In a second aspect of the invention, there is provided a system according to the claimed invention operable to monitor a telecare customer within a customer dwelling comprising a plurality of associated sensing nodes each of which is operable to sense events associated with the customer's activities within the customer dwelling, and a gateway device connected to each of the associated sensing nodes for receiving sensed data therefrom, the gateway device incorporating the determining means.

Preferably, the reference threshold values are established by nodes which have already gone through a full learning or training period and which already have associated with them established threshold values for reference by the newly-installed node. Such threshold values may alternatively be obtained from yet even-earlier nodes, and so on.

In a third aspect of the invention, there is provided a gateway device for use in a system according to the second aspect of the invention which is operable in use, to receive sensed data from a plurality of associated sensing nodes and to receive identified reference threshold values from a remote identifying means, and incorporating determining means for determining if, upon one of the sensing nodes sensing an event, the time period after the sensing node has sensed the event exceeds a respective threshold value before a further event is sensed by one of the said sensing nodes.

The sensing nodes can be configured to communicate directly with a database which holds threshold values already established by the established nodes, to enable the newly-installed node to obtain the threshold value most closely corresponding to the data sensed by the new node during its learning phase. More preferably however, a gateway device, which communicates with the new sensing node and the database (which can be located locally or remotely to the new node) obtains the appropriate threshold value for the new node. The gateway device holds this threshold value for the particular new node, and upon the new node sensing a further event, the sensed data of the further event is sent to the gateway which performs a comparison to determine of the time period elapsing after the sensed event exceeds the threshold obtained from the database. The gateway can be configured for some or all the sensing nodes in the dwelling or premises of the customer, so that the threshold appropriate to each node is obtained from the database and held by the gateway device for the node concerned. This further allows for the gateway to collate the data sensed by each node which it is connected to, and to provide a more holistic view of the activity levels and behavioural patterns by the customer within the dwelling.

In a fourth aspect of the invention, there is provided a method for determining if a time period after a sensing node has sensed an event exceeds a threshold inter-event time interval, including the steps of establishing a plurality of reference threshold values, wherein each reference threshold value is associated with a set of reference inter-event time intervals or metrics statistically derived therefrom, calculating a set of preliminary inter-event time intervals based on the sensing of a plurality of events by the sensing node, comparing the set of preliminary inter-event time intervals or metrics statistically derived therefrom, with each set of reference inter-event time intervals or metrics statistically derived therefrom, identifying the reference threshold value associated with the set of reference inter-event time intervals or metrics statistically derived therefrom being the closest match to the set of preliminary inter-event time intervals or metrics statistically derived therefrom, and upon the sensing node sensing a further event, determining if the time period after the sensing node has sensed the further event exceeds the identified reference threshold value before a yet further event is sensed either by the sensing node or an associated sensing node.

In the invention, a node can be newly-installed but still be capable of functioning to detect abnormal time intervals indicating a problem, either immediately upon installation or relatively quickly, by referring to a threshold value it need not establish for itself.

A newly-installed node can also be set up to go through a learning period wherein all data gathered from the events it detects go solely or mainly to setting a threshold value for its own use. As mentioned above, establishing a threshold value in this way will take a longer time than the method wherein the new node uses a value obtained from an established node which exhibits the same or similar event detection pattern as the new node.

In the invention, the method of detecting an excessively long time interval between sensed events indicating a possible cause for concern, is carried out by the new detection node by reference to a threshold value which it has not learned for itself.

The threshold value can be dynamically and automatically re-established or refreshed as the node continues detecting events. This allows for the threshold value, initially obtained from an established node, to be honed to greater accuracy. In one embodiment, such improvements could be communicated back to update the threshold values associated with the established nodes.

In the event that no reference to threshold values by established nodes is possible, the initial establishment of a threshold value may take longer. However an adaptive approach to dynamically set threshold values allows for greater customisation and personalisation to the particular function of the node, its location and the activities of the specific telecare customer. In this way, use of an adaptive method is an improvement on current methods where a static threshold value is manually set (and re-set) for nodes. Furthermore it is useful in the context where a network of nodes may not be available e.g. where there is lack of network connectivity, or where only the one node is needed.

BRIEF DESCRIPTION OF THE DRAWINGS

Embodiments of the invention will now be described by way of example only with reference to the accompanying drawings in which.

DETAILED DESCRIPTION OF PRESENT EXAMPLE EMBODIMENTS

Figure 1:
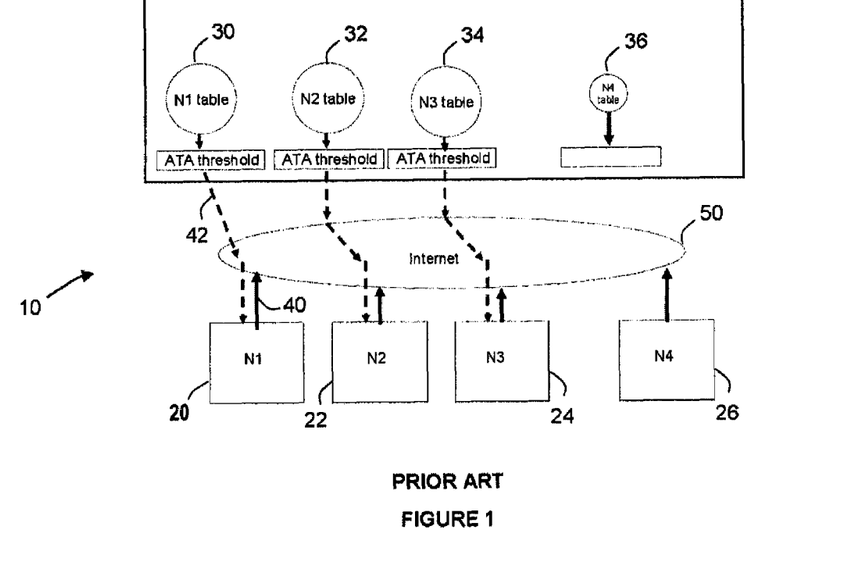
FIG. 1 is a schematic depiction of the components of a prior art telecare system.

FIG. 1 is a schematic depiction of a telecare system architecture (10) which is based on the adaptive approach using an Adaptive Threshold Algorithm (ATA). Here, nodes or sensors (20, 22, 24 and 26) are placed at various locations within the customer's home. A typical installation comprises 20 sensing nodes. The sensor nodes are connected to wired or wireless transmitters which communicate with a monitoring unit, which is typically located within the customer's premises. This monitoring unit may comprise a single board computer which hosts a telecare software client, which determines if a sensed event (or time interval between positive events) is an abnormal event giving cause for concern. A preferred embodiment of the telecare software is one which takes into account the fact that activity levels and patterns will vary depending on the time of day, the room in which the sensor is located, and the lifestyle of the individual customer.

In FIG. 1, "established" nodes N1 to N3 (20, 22, 24) have already been in use for some time and so have completed their learning stage, and already gathered a certain amount of sensed inter-event data. The data thus obtained is fed to (arrow 40) and stored in historical data tables (30, 32, 34) corresponding with each node. Based on the data from a certain node, an ATA threshold value associated with that relevant node is determined.

To establish an ATA value according to conventional methods, a node must have accumulated a minimum amount of data during its learning period stage. An ATA value is typically generated in the following manner.

First, inter-event time data gathered by a node over the initial learning period is collated. As noted above, the learning period is the time during which the node is simply gathering data about sensed events, as it cannot yet sense non-events.

Figure 6:
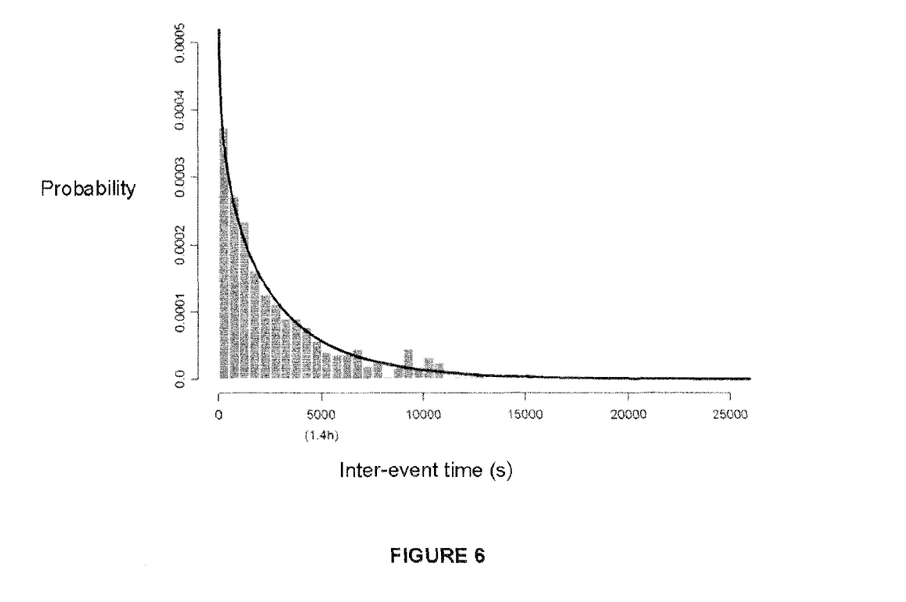
FIG. 6 is a graph depicting incidences of inter-event times for a node in the telecare system over a time period.

Such data may be filtered to remove outline data, which is then used to create a statistical description of the data, examples of which may be:

Relevant statistical descriptive parameters e.g. mean values, standard deviations (SDs), or Relevant distribution fitting parameters which are calculated by fitting the node data to a statistical distribution using known curve fitting techniques as illustrated in FIG. 6, such as maximum-likelihood or other regression methods.

A measure of abnormality is then calculated, for example by looking at:

A specific number of SDs from the mean,

A minimum probability of matching a fitted distribution, or

Previously observed and known abnormal events, e.g. those reported by the customer.

A threshold value is then set for the inter-event times corresponding to this level of abnormality.

It is possible to obtain different sets of different threshold levels, by using different abnormality measures, so that a single system can be operated using thresholds of different sensitivity levels, for example, if it is desirable for the system to have low priority and high priority alarms.

The relevant node is informed (arrow 42) of its ATA threshold, which determines when an event (or non-event) should cause the Telecare system to raise an alarm. In the embodiment shown, the architecture includes a network (50) so that the node tables (30, etc.) are depicted as being located remotely from the nodes (20, etc.) which are located within the customer's home. However network in this prior art architecture serves mainly to reduce the complexity of the equipment within the home by moving part of it (e.g. the historical data table) offsite. The ATA functionality could be provided at any location, e.g. locally at the nodes within the customer's home without the need for network connectivity to remote locations.

In the example of FIG. 1, node N4 (26) is one which is newly installed in the customer's house. It has either gathered no or little data. Until and unless it gathers the minimum necessary amount of historical data, its corresponding historical data table (36) is not (fully) populated, and no ATA threshold values can be determined nor set for node N4. Until an ATA threshold is set for it, node N4 is still in a learning stage, and is functionally useless (or at least unreliable) for the purpose of accurately recognising a negative event signifying an abnormal situation.

In this system, the data gathered by each node (20, etc.) is used only by that node. This is logical given that each customer has habits, routines and behaviour unique to him or her. Moreover, different customers live in different houses with different layouts which would affect behaviour, and thus the data gathered by each node placed around the house should only be applicable to that node in determining whether a sensed event is abnormal or not. The data gathered by, and crucially the learning process of, each node, is deemed to be independent from other nodes. In certain cases, a group of nodes (e.g. a cluster within close proximity of each other, such as within a single dwelling, or within a room or a corridor of the dwelling) can work together to obtain a composite picture of the customer's behaviour, but even in these situations, the learning and ATA thresholds of the group of nodes are treated separately from other groups of nodes or individual nodes.

The applicant has however, in its activities in the telecare field, realised that while there are certainly differences in behaviour patterns between customers, they nonetheless share a great many similarities. Of particular interest is the fact that identical or similar inter-event time data can be gathered from different nodes. Because some nodes in the system are already established and have an ATA threshold value already associated with it, a new node could leapfrog much of the learning process by adopting the threshold value of such an established node.

Figure 2:
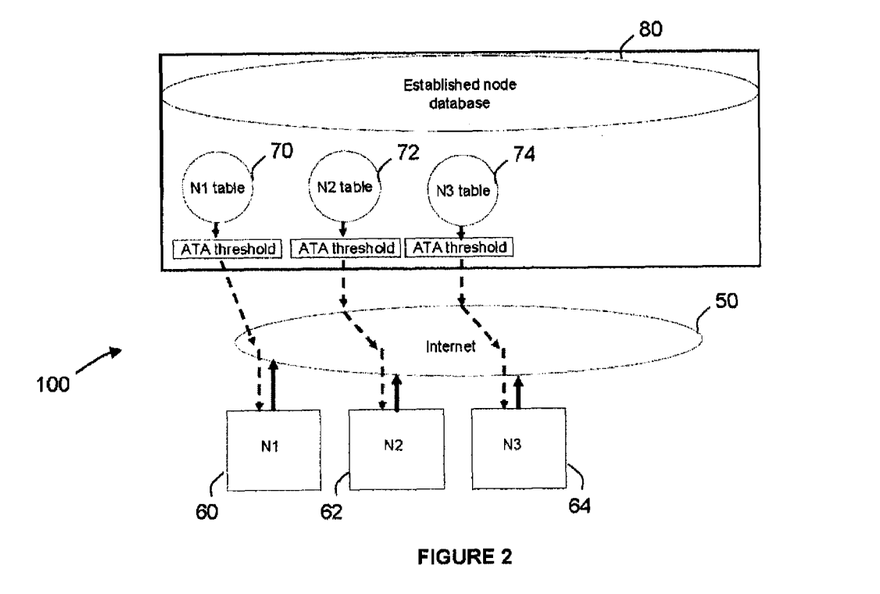
FIG. 2 is a schematic depiction of established nodes in a telecare system of the invention.

Based on this realisation, the architecture of a telecare system (100) of the invention depicted in the schematic view of FIG. 2 reflects the new approach and is thus set up differently from known ATA methods. Its chief characteristic is that historical data of each node is centralised into a database, allowing for it to be shared between nodes (60, 62, 64, 66) within the network. This arrangement addresses the need to cut short or to do away with a long learning lead-in period for "new" node N4 (66) to establish its own ATA threshold value via the "ATA approach or route", before it becomes reliably functional, i.e. able to detect negative events as well as positive events.

Figure 3:
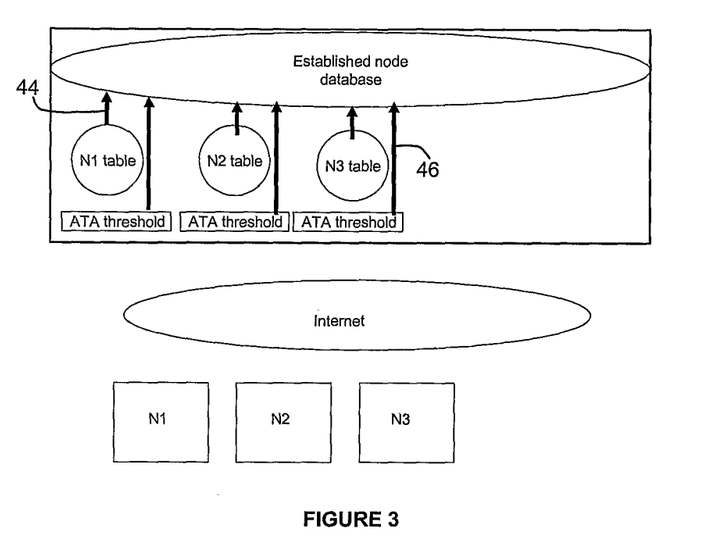
FIG. 3 is a schematic depiction of the storage of established node data.
Figure 7:
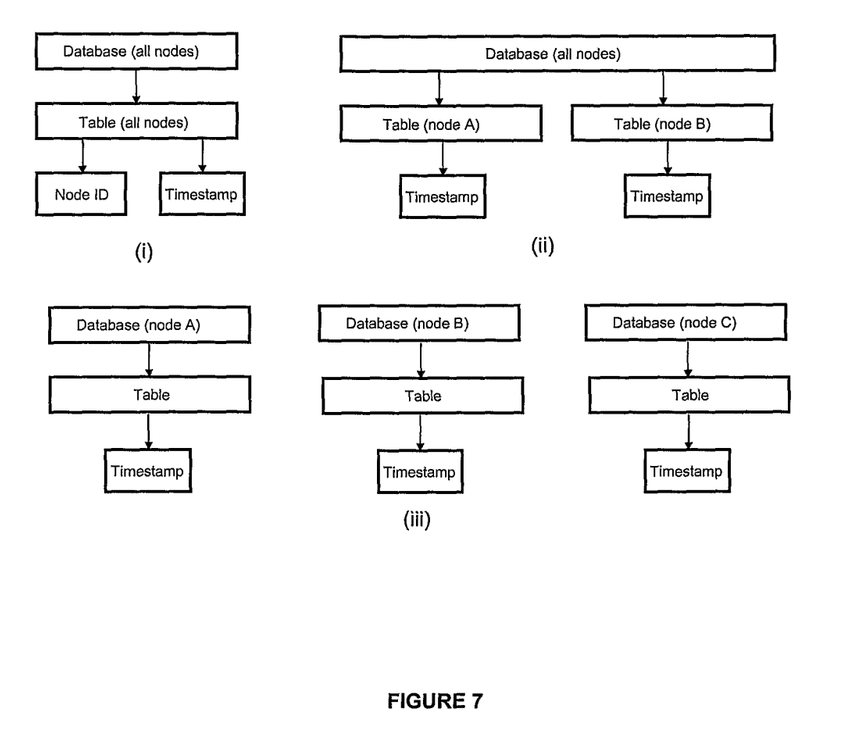
FIG. 7 depicts variations in database configurations within the telecare system.

In the invention, the nodes are placed within the customer's home in the conventional way. As shown in FIG. 2, each established node (60, 62, 64) is associated with historical data tables (70, 72, 74) and its own ATA threshold figure. In practice, the established nodes (of which there could be hundreds or thousands in a typical system) have gathered a great deal of historical information, which in the invention is centralised (arrows 44 and 46) into an established node database (80) as shown in FIG. 3. The historical information can be classified according to e.g. its inter-event time value. Historical information can be all contained in a single database (80) although different historical data types and sets can be separated into different databases. As shown in FIG. 7 below, data can be held in a single database with unique identification numbers to differentiate between different nodes in (i); alternatively all data can be held in a single database but in different tables (ii); or in (iii), data can be held in separate databases, which may even be held at different remote locations.

Figure 4:
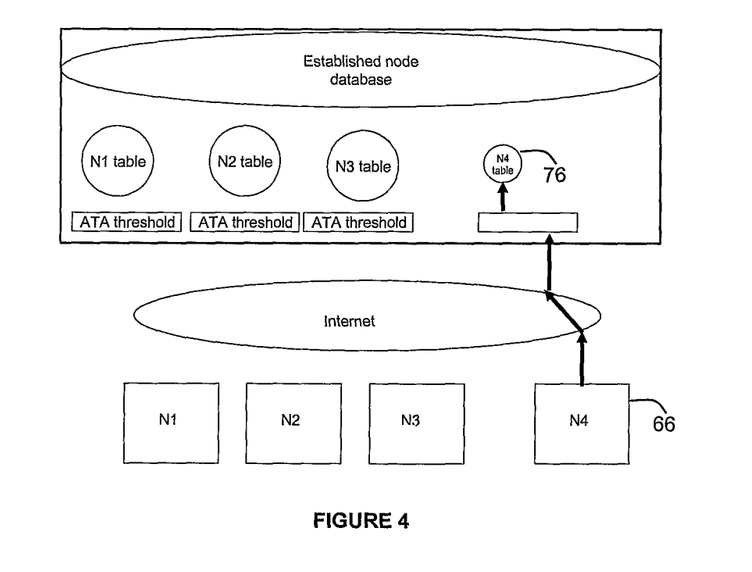
FIG. 4 is a schematic depiction of a newly-installed node in the telecare system.

In FIG. 4, node N4 (66) is newly-installed, and does not yet have its own ATA threshold value. A typical process involved in the establishment of an ATA value for a new node will now be described. The new node N4, once installed, undergoes an initial data-gathering stage wherein it senses and logs positive events it senses. Once it has gathered a certain amount of inter-event data, it is possible to perform a comparison of the data it has gathered, with that in the database (80), to find the most similar set of historical data. The ATA threshold value associated with the most similar historical data set is adopted and set for the new node. This method is within this description termed the "CBR approach" or "CBR route" although the skilled person would appreciate that this method need not be carried out using the CBR technique in particular.

Figure 5:
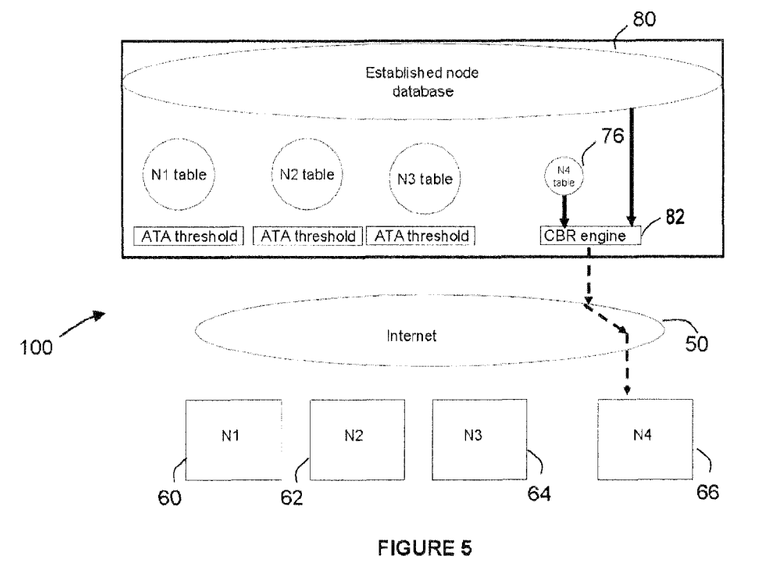
FIG. 5 is a schematic depiction the setting of a threshold value for the new node.

As shown in FIG. 5, a CBR (case based reasoning) engine (82) can be used to help determine if a historical data set is the best or closest match to the data obtained by the new node in its initial data-gathering stage. As is known in the art, CBR is the concept of solving new problems based on solutions to past similar problems, by drawing upon a bank of existing information.

The initial data-gathering period of the CBR approach is superficially similar to the learning period of the prior art ATA approach, but is different in that the purpose is not to gather enough information to establish its own ATA threshold value, which will take much time. Instead, the purpose is to identify the most-similar historical data set with the aim to adopting the threshold value associated with that historical data set. This potentially cuts out much if not all the learning time otherwise needed by node N4 to become established through the sensing and gathering of its own historical data, to allow node N4 to take on the function of sensing negative events which may signify an abnormality. This is because the new node need not undergo the full training period required in prior art systems. Instead it undergoes a shorter period of initial data-gathering, which requires only enough data to allow the ATA threshold value associated with a set of similar inter-event data to be selected and set using e.g. CBR techniques as more fully described below.

The skilled person would of course be aware that the new node N4 could in a preferred embodiment, refine its assigned ATA threshold attributed to it with data the node continues to collect.

Figure 8:
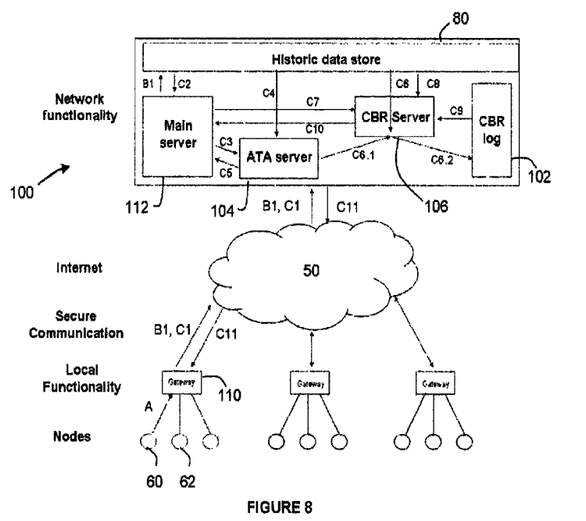
FIG. 8 shows the primary data flows within the telecare system.

The sharing of historical data in this fashion requires that nodes be networked in some fashion, which could take the form of the Internet or some smaller local network (50) as shown in FIG. 8. The emphasis is thus shifted away from data gathered by individual nodes. The underlying assumption of this network-centric approach is that if inter-event data gathered by newly-installed sensor nodes resembles historical data obtained by established nodes, the threshold values associated with the established nodes can usefully and reliably be adopted for the new node. This can be contrasted with conventional telecare systems, where each node is required to gather enough data to establish its own threshold values. As noted above, this requires much time and in the case of some nodes, may never progress beyond the learning period even after years.

In a typical telecare system where the sensor devices are made by different manufacturers, node operation may differ. It is possible to overcome any issues on this front by mapping the characteristics of the various nodes, by obtaining product specifications for the nodes from the manufacturers, and testing the new nodes against the older more established nodes. The characteristics can be used as part of a filter between the gathered node data and the CBR algorithm. The filter can be used to ensure interoperability of different types and makes of nodes with the existing database of nodes.

The CBR engine is preferably configured to balance the need for node and system sensitivity (i.e. the ability to quickly raise an alarm) and reliability by using e.g. decision theory.

An implementation of a specific embodiment of the invention will now be described in detail, using actual data gathered from a trial, case studies of which were published in "Case Studies from the Liverpool Telecare Pilot" (supra) to simulate the results that might have been obtained by using the invention. Specifically, the data was collected from a sample of about 300 nodes deployed in 21 customers' homes.

Essentially, the implementation involves initial decisions about how to describe variations in inter-event interval data gathered by each node, and how much of such data is required of a node to set its own ATA threshold. These decisions help set the parameters for the generation of ATA values which are stored in the established node database. Subsequently, it is decided if the new node has sensed a sufficient number of events to set its own ATA threshold value; if it has not then it may refer to a suitable threshold value in the established node database.

Figure 9:
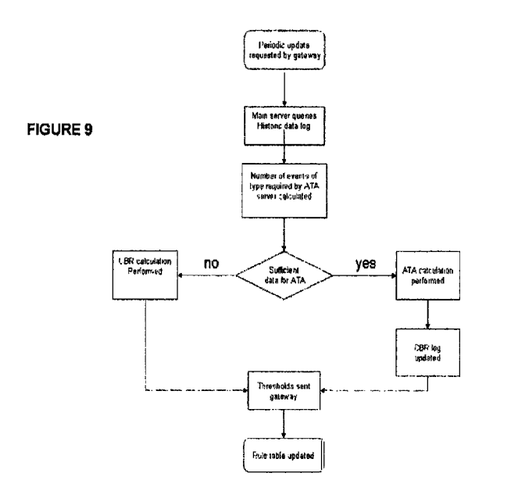
FIG. 9 is a flow chart of the server processes.

FIG. 8 shows the primary data flows within the system, and FIG. 9 shows the server route flows of this exemplary embodiment.

1. Establishing the Parameters for the Generation of ATA Threshold Values

The following preparatory set-up steps are carried out for each new system installation, which affect the generation of threshold values for storage in the established node database.

As a preliminary, data of a certain number of inter-event intervals is already available, e.g. data from established nodes, from pre-service trials of the system or in the form of simulated data based on test installations.

The first preparatory task is to decide how to describe variations in the inter-event data obtained by each node in the installation, by using one or more of a number of statistical metrics described below. The metrics are chosen by reference to preliminary data already available. A set of metrics is used to describe the variation in the inter-event interval data collected by the nodes. Preferably, a metric should highlight the variability in the inter-event interval data, so it should be selected based on its likelihood to have a significant bearing on the threshold value setting for a particular node, which in turn depends on the type of inter-event data in question. This means selecting a metric which usefully describes the type of activity sensed by a particular node. For example, a PIR's field of view can encompass partial or multiple physical rooms in a dwelling, as well as a single room. It is also worth noting that these metrics do not have to be based solely on sensor data, but may include those which describe other influential factors such as the age of the customer (potentially related to mobility), the time of day, the size of dwelling, etc.

Preferably the selected metrics should avoid descriptive parameters based on single readings and make use of more robust statistical measures. Examples of possible data based statistical metrics are:

Mean daily node events
Number of arrivals
Mean inter-event time
Inter-event standard deviation
Inter-event skewness
Inter-event kurtosis Preferably, at least one of the parameters should indicate the spread of the data. This is due to the need to incorporate a measure which acknowledges that the node events may not come from a simple distribution with similar spread across nodes. The applicant has in its experience noted that standard deviation was also particularly useful to statistically describe the inter-event interval data.

The statistical descriptions, together with the ATA threshold values associated with each node, is stored in a established node database, here referred to as a CBR log (102).

To simplify the process of deciding which metric to choose to describe the inter-event interval data, it is possible to reduce the number of metrics to be considered. For example, a principal component analysis (PCA) could be carried out to identify a smaller subset of metrics which may be used to explain the majority of variability in the data. As known in the art, the PCA involves a change of basis which uses projections of data which have maximum variability. As noted above, the applicant's experience was that the inter-event mean and inter-event standard deviation were found to be the most suitable for describing variability in the data. The example embodiment described here uses these two metrics.

A CBR log (102) is generated containing the chosen statistical metrics. The metrics are chosen by reference to preliminary data already available, and used to provide a description of the data associated with each node (as described below) and the appropriate ATA threshold values for each node. Although it is possible for the system to start operation with no stored data in the CBR log, it is preferable to use any existing data available.

The second preparatory task is to decide on the minimum number of sensor events required by the ATA server (104) (described in detail below) of a node before it can be relied upon to generate a ATA threshold value which will enable the node to detect an abnormal time interval which may raise an alarm. Determining this minimum number may involve a sensitivity calculation. The applicant plotted sample size of nodes vs. threshold variation to arrive at an evidence-based figure. In this example, where data was collected from a sample of about 300 nodes deployed in 21 customers' homes, the applicant as set the ATA server (104) to use as a minimum number of 100 sensed events, so that when the node has sensed 100 events, a threshold value can be set for that node using its own sensed data, using the ATA approach and without the need to refer to the established node database. If fewer than 100 events have been detected, it is nonetheless possible to set a threshold value for the node using the CBR approach of the invention, by using a suitable threshold value stored in the established node database.

2. Normal Daily Operation

When the above preparatory steps are complete, the "normal" daily operation of the system can commence. With reference to FIG. 2, the nodes (60, etc.) have been set in place within the customer's dwelling. The gateway device (110) streams the sensor events detected by the nodes (60, etc.) back to the main server (112). The main and other servers perform the computation required to generate a threshold value using the ATA method, from sensed data from nodes. The server is preferably located within the system at a location remote of the dwelling. The threshold value is associated with the sensed data (comprising positive events as well as inter-event intervals) and stored in the historic data store (80). Once initial ATA threshold settings have been set for a particular node, the gateway device compares sensed data from the node against threshold value data for that node to detect abnormal periods of inactivity.

The gateway device is a central controlling device to which the nodes send all sensed data, and comprises a rules-based engine which raises an alarm if the data sent by any node exceeds the threshold value for that node. In the present embodiment, the gateway device sits within the dwelling, and its function can be performed by an Internet hub. The gateway device can be located within the premises, or outside the premises. It is possible for the gateway functions to be carried out by each node although this would make the nodes very power-hungry.

A pre-defined period after installation of a new node, say after 14 days, it is assumed that the new node has sensed at least a few events. At this time, the gateway requests (arrow C1) a threshold value associated with the new node via the network (50), from the main server (112). The server queries the historical sensor event log(arrow B1) and makes a decision, outlined in FIG. 9, depending on whether the new node has sensed the minimum number of sensed events required by the system, whether to set the threshold value for the new node using the ATA process or the CBR process.

If there are a sufficient number of sensed event data gathered by the new node (100 or more, in the present example), the main server requests (arrow C3) a threshold value from the ATA server which computes the threshold value being a statistical description of the sensed data obtained by the new node. The ATA server retrieves the sensed data for the new sensor node (arrow C4), calculates its threshold value and returns (arrow C5) this to the main server. After successfully setting an ATA threshold value for the new node, the ATA server notifies (arrow C6.1) the CBR server (described in greater detail below) of this value. The value allows the CBR server (106) to query the historic data store (80), receiving back (arrow C4) the historical sensed data for the node, from which it can calculate the required metrics. The threshold and metric combination is then registered (arrow C6.2) with the CBR log.

If there is insufficient sensed event data (here, less than 100) for the new node to perform an ATA calculation, the main server requests (arrow C7) a threshold value from the CBR server. The CBR server calculates the descriptive metrics by pulling (arrow C8) historic sensed event data from the historic data log and determines which threshold value is applicable to the new node, by comparing the sensed event data gathered by the new node, with the historical sensed data which has been classified into one of a number of threshold classes, which shall be described below. The CBR server return (arrow C10) a threshold value to the main server, this threshold value being associated with the historical sensed data which is the closest match to the sensed event data gathered by the new node.

The main server sends (arrow C11) the identified threshold value to the gateway device (110), via the network. The gateway device updates its locally held threshold value rule table and starts monitoring to sense inter-event intervals which exceed the threshold value.

As the new node continues sensing events, data relating to these can continue to be sent to the gateway, to refresh and update the threshold value attributed to the node. The home gateway will periodically request threshold value updates from the main server at periodic intervals, but only those nodes with more than the minimum number of sensed events for an ATA calculation will generally be supplied with an updated threshold value. It is possible to automatically update the CBR thresholds periodically also, but the system administrators may prefer to keep these values constant between automatic or manual resets.

The following describes in more detail the main functions for the CBR and ATA servers.

CBR Server

The CBR server performs two main functions. The first is to calculate and store established node threshold values and the corresponding metrics. In the present example, two subsets can form the established node sensed event data set:
1. Nodes with sufficient sensed events (100 or more) to set a threshold value using the ATA method; and
2. Nodes which have not sensed a single event above a predetermined lowest threshold category (e.g. 30 min) in a specified period e.g. 90 days.

The second subset describes nodes for which a threshold value may never be set using the ATA method because of insufficient event data. It is preferable to attribute a minimum threshold value to such nodes, rather than to leave such nodes without a threshold value at all, provided that the data does not show that an excessive number of alarms would be raised (e.g. more than one every 90 days). When new nodes satisfy either of these criteria, they may be included in the CBR log.

Although it is possible to store the threshold values in the CBR log(102) as continuous value data, they are more preferably grouped into discrete classes as shown below. Each threshold class has a discrete threshold value associated with it. Table 1 below shows those used in the present example:

TABLE 1

CBR log classification classes

| Threshold Class | Threshold value |
|---|---|
| 0 | 30 min |
| 1 | 60 min |
| 2 | 3 hours |

TABLE 1-continued

CBR log classification classes

| Threshold Class | Threshold value |
|---|---|
| 3 | 6 hours |
| 4 | 12 hours |
| 5 | 24 hours |

The classification of the threshold data allows a linear discriminant analysis (LDA). As known in the art, LDA is a technique for data classification and dimensionality reduction. Classifying the data also allows the system administrator to have better visibility of the threshold value data. Other approaches to this end are also possible: for example, a nearest neighbour approach could be used where the threshold value for a new node is simply taken to be equal to that associated with the closest-matching set of metrics, e.g. mean and SD.

The second function of the CBR server, in the present embodiment, is to calculate metrics for the new node. (However in alternative embodiments the metrics could be calculated by the node or its associated gateway device, rather than by the CBR server.) When a new node, or node group, is introduced to the network there will be a short period (14 days in the present example) between installation of the node and commencing the detection of abnormal time intervals. This period could be the first 14 days after node installation, or else be incorporated as part of the care provider's telecare installation protocol. A typical protocol includes undertaking, in the present example, a two-week review preceding installation to ensure the system is functioning as intended and the customer is happy with the monitoring system. The end of the two-week review, a timely point at which to switch on the personalised threshold value for the new node (i.e. initiate a request for a threshold value as shown by arrow C1 in FIG. 8). At this point the system is required to make a decision on which of the two threshold setting methods—the ATA route or the CBR route—is appropriate for the new node, as discussed above in connection with FIG. 9.

The operation of the CBR server, in the present embodiment, to identify a threshold for a new node based on a preliminary set of measurements by the new node, by comparison with measurements made by established reference nodes can thus be summarised thus. The preliminary measurements are categorised according to the time of day at which the first event in the inter-event interval is detected (i.e. inter-event intervals commencing between 00:00 and 02:00 are assigned to the 00:00-02:00 category, etc.) and all of the intervals in each category are then analysed to obtain statistical metrics therefrom, in particular, in the present embodiment, the mean interval duration and the standard deviation of the measured interval durations within each category. Within the CBR server, each set of historical data (e.g. a set of measured inter-event interval durations within a particular time category (e.g. 00:00-02:00) as measured by a particular node) which gave rise to a determination of a threshold value by the ATA method, is placed into a threshold class based on the threshold value determined by the ATA method (i.e. all sets of data giving rise to a determination of a threshold value of up to and including 30 minutes are placed in threshold class 0, all sets of data giving rise to a determination of a threshold value of between 30 and 60 minutes are placed in threshold class 1, etc.); each set of historical data is then analysed to obtain reference statistical metrics therefrom (i.e. a mean and standard deviation is calculated for each set of historical data such that each threshold class has associated with it a number of pairs of reference mean and standard deviation values). The statistical metrics derived from the preliminary data of the new node whose threshold is to be determined by the CBR server is then compared with the sets of reference metrics associated with each threshold class using the LDA technique in order to categorise the metrics associated with the new node as belonging to one of the threshold classes (note, as mentioned above, LDA typically generates a probability of the metrics belonging to each of the possible classes; in the present embodiment, this probability is converted into an actual class by simply selecting the class with the greatest probability of membership assigned to it—in the event of two or more classes having equal probabilities, the higher class is selected), and then the threshold associated with the particular selected threshold class is identified as the new threshold to be assigned to the new node.

Tables 2 and 3 depict comparative results. Table 2 shows the time taken for the ATA thresholds to be set using gathered data and Table 3 shows thresholds set based on 14 days' data using methods of the current invention.

TABLE 2

Time taken for threshold values to be set

| Room | Time period | Weeks to set | Threshold value (hours) |
|---|---|---|---|
| Bedroom | 00:00-02:00 | 8 | 5.2 |
|  | 02:00-04:00 | 6 | 4.1 |
|  | 04:00-06:00 | 6 | 4.7 |
|  | 06:00-08:00 | 15 | 2.3 |
|  | 22:00-00:00 | 5 | 4.3 |
| Lounge | 08:00-10:00 | 5 | 2.0 |
|  | 10:00-12:00 | 5 | 2.9 |
|  | 12:00-14:00 | 7 | 2.5 |
|  | 14:00-16:00 | 7 | 3.5 |
|  | 16:00-18:00 | 8 | 3.1 |
|  | 18:00-20:00 | 6 | 2.2 |
|  | 20:00-22:00 | 6 | 1.6 |

Referring to Table, 2, threshold values work in the following manner. When an event is first sensed within the dwelling, the telecare system will check against a table such as Table 2, to determine in which time period the sensed event occurred. If it occurred, say, in the lounge at 15:00, the threshold value of 3.5 hours means that the system expects to sense another event within the dwelling by 18:30. If no event is sensed, then this is deemed by the system to be an abnormal or negative event, possibly being cause to raise an alarm. If no event is sensed within a time period however, then that threshold value is not used. Thus, to continue the example above, the system expects for an event to be sensed by 18:30, but the applicable threshold value of 2.2 hours in the time period of 18:00 to 20:00 itself is not activated, as the last sensed event did not occur within that time period. If, however, a subsequent event was to be sensed at 17:00, then the abnormal period detection timer is re-set for 3.1 hours from 17:00—i.e. a new event is expected by 20:06.

There are a variety of ways to accommodate the situation where the customer leaves the dwelling, so that there may not be an event to sense after the last sensed event. For example, a sensor on the front door, or a door mat, could record the fact that the customer is no longer in the house and that no subsequent sensed event should be expected, thus deactivating the threshold value that has been set by the last sensed event. Alternatively, the customer could manually turn the system off in his absence.

In Table, 2 the threshold values set for the nodes in the bedroom and the lounge were set after at least an initial learning period that lasted more than a month. In the case of the node in the bedroom, the learning period was complete only after 15 months. In many other cases (the time periods which are missing from the table above e.g. 08:00 to 22:00 in the bedroom), an insufficient number of events were sensed so that even after years, a threshold value could not be set using the ATA method.

Using the CBR approach based on the first 14 days' of data, threshold values were estimated and set for each node and for all time period as follows:

TABLE 3

Threshold values (in hours) set using the CBR approach

| | Time period | | | | | | | | | | | |
|---|---|---|---|---|---|---|---|---|---|---|---|---|
| | 00-02 | 02-04 | 04-06 | 06-08 | 08-10 | 10-12 | 12-14 | 14-16 | 16-18 | 18-20 | 20-22 | 22-00 |
| Bedroom | 24 | 24 | 24 | 3 | 0.6 | 0.9 | 0.5 | 0.6 | 0.6 | 0.6 | 0.6 | 6.0 |
| Hall | 0.5 | 0.5 | 0.6 | 0.6 | 0.6 | 0.6 | 0.6 | 0.6 | 0.6 | 0.6 | 0.6 | 0.6 |
| Kitchen | 0.5 | 0.5 | 0.5 | 0.5 | 0.6 | 0.6 | 0.6 | 0.6 | 0.6 | 0.6 | 0.6 | 0.6 |
| Lounge | 0.5 | 0.5 | 0.5 | 0.7 | 6.0 | 3.0 | 6.0 | 6.0 | 6.0 | 6.0 | 6.0 | 3.0 |
| Toilet | 0.5 | 0.5 | 0.6 | 0.6 | 0.6 | 0.6 | 0.6 | 0.6 | 0.6 | 0.6 | 0.6 | 0.6 |

As can be seen, it can be expected that threshold values can be set for all time periods in all the rooms, only two weeks after installation in a customer's dwelling using the CBR approach.

Where the classification approach adopted is linear discriminant analysis (LDA), the method returns the probability of membership for each class, as well as the predicted class for the new nodes. Use of this technique is thus preferred as a threshold value can be set based on a mixture of data from the available classes.

The next table shows the applicant's experience in using a system according to the invention. It was found that an excessive number of alerts was not generated by early threshold setting using the CBR approach. The one period which could give concern was the Bedroom between 06:00-08:00 when 5 additional alarms were generated. However, when a comparison is made between the CBR-generated threshold of 3 hours and the corresponding threshold value which would have been obtained by the ATA method (after 15 weeks) at 2.3 hours it may be seen that the CBR threshold exceeds the ATA threshold and the increased number of alarms is purely because the system has been operational for longer (an extra 13 weeks).

TABLE 4

Additional alarms generated in 467 days

| | Time period | | | | | | | | | | | |
|---|---|---|---|---|---|---|---|---|---|---|---|---|
| | 00-02 | 02-04 | 04-06 | 06-08 | 08-10 | 10-12 | 12-14 | 14-16 | 16-18 | 18-20 | 20-22 | 22-00 |
| Bedroom | | | | 5 | 2 | 1 | 1 | | | | | |
| Hall | | | | | | 1 | 3 | | | | | |
| Kitchen | | | | | 3 | | | 2 | 1 | | | |
| Lounge | | | | | 1 | 2 | 2 | | | | | |
| Toilet | | | | | | | | | | 1 | | |

ATA Server

The ATA server performs the following roles:
1. Obtains (arrow C4) the historic data set from database;
2. Fits a probability distribution to the data;
3. Uses a decision theory based approach to determine the appropriate threshold value; and
4. Reports (arrow C5) these threshold values back to the main server and also the CBR server.

The threshold values can then also be stored (arrow C6) in the CBR log and downloaded (arrow C11) to the gateway for use.

The methods and configurations as described above and in the drawings are for ease of description only and not meant to restrict the apparatus or methods to a particular arrangement or process in use. It will be apparent to the skilled person that various sequences and permutations on the methods and apparatus described are possible within the scope of this invention as disclosed.

The methods and apparatus described herein may also be used in a variety of contexts, i.e. not only or exclusively within or for a telecare system. Thus they may be usefully deployed in any system for detecting positive events, and negative non-events, where thresholds can be set based on time or other similar criteria, for example in a production line.

What is claimed is:

1. A system for determining if a time period after a sensing node has sensed an event exceeds a threshold value, including
   establishing means for establishing a plurality of reference threshold values, wherein each reference threshold value is associated with a set of reference inter-event time intervals or metrics statistically derived therefrom,
   calculating means for calculating a set of preliminary time intervals or metrics statistically derived therefrom, based on events sensed by the sensing node,
   comparing means for comparing the set of preliminary inter-event time intervals or metrics statistically derived therefrom, with each set of reference inter-event time intervals or metrics statistically derived therefrom,
   identifying means for identifying the reference threshold value associated with the set of reference inter-event time intervals or metrics statistically derived therefrom, being the closest match to the set of preliminary inter-event time intervals or metrics statistically derived therefrom, and
   determining means for determining if, upon the sensing node sensing a further event, the time period after the sensing node has sensed the event exceeds the identified reference threshold value before a yet further event is sensed by the sensing node or an associated sensing node.

2. A system according to claim 1 wherein the identifying means is configured to identify a plurality of reference threshold values each of which is associated with a time of day period, and wherein one of the plurality of reference threshold values is selected for use by the determining means in dependence on the time of day the further event is sensed by the sensing node.

3. A system according to claim 1, wherein the establishing means comprises a plurality of reference nodes configured to sense the sets of reference inter-event time intervals with which each reference threshold value is associated.

4. A system according to claim 1, wherein the plurality of reference threshold values are stored in a database, and wherein the establishing means, the database, the comparing means, the sensing node, the identifying means, and the determining means are connected via a network.

5. A system as claimed in claim 1, operable to monitor a telecare customer within a customer dwelling comprising a plurality of associated sensing nodes each of which is operable to sense events associated with the customer's activities within the customer dwelling, and a gateway device connected to each of the associated sensing nodes for receiving sensed data therefrom, the gateway device incorporating the determining means.

6. A system according to claim 1, wherein the sensing node and any reference nodes are sensing or metering devices configured to sense as an event, a change in a physical property or use of a utility or other resource including any one or more of water, sewer, water, gas, electricity, or telephone services.

7. A gateway device for use in a system according to claim 5 operable in use, to receive sensed data from a plurality of associated sensing nodes and to receive identified reference threshold values from a remote identifying means, and incorporating determining means for determining if, upon one of the sensing nodes sensing an event, the time period after the sensing node has sensed the event exceeds a respective threshold value before a further event is sensed by one of the said sensing nodes.

8. A method for determining if a time period after a sensing node has sensed an event exceeds a threshold inter-event time interval, including the steps of establishing a plurality of reference threshold values, wherein each reference threshold value is associated with a set of reference inter-event time intervals or metrics statistically derived therefrom, calculating a set of preliminary inter-event time intervals based on the sensing of a plurality of events by the sensing node, comparing the set of preliminary inter-event time intervals or metrics statistically derived therefrom, with each set of reference inter-event time intervals or metrics statistically derived therefrom, identifying the reference threshold value associated with the set of reference inter-event time intervals or metrics statistically derived therefrom being the closest match to the set of preliminary inter-event time intervals or metrics statistically derived therefrom, and upon the sensing node sensing a further event, determining if the time period after the sensing node has sensed the further event exceeds the identified reference threshold value before a yet further event is sensed either by the sensing node or an associated sensing node.

9. A method according to claim 8 wherein the steps are iterated to identify a plurality of reference threshold values each of which is associated with a time of day period, and wherein in the determining step, one of the plurality of reference threshold values is selected for use by the determining means in dependence on the time of day period the further event is sensed by the sensing node.

10. A method according to claim 8 wherein the metrics established in the establishing step comprises at least a standard deviation of a reference range of time interval values formed from the reference inter-event time intervals.

11. A method according to claim 8, wherein the identifying step includes use of a statistical or a probability analysis technique to identify the closest match between the set of reference inter-event time intervals and the set of preliminary inter-event time intervals.

12. A method of monitoring a telecare customer according to claim 8, wherein a lack of wellbeing of the telecare customer is indicated when the time period after the further event exceeds the identified reference threshold value, and further 'including a step of raising an alarm upon determination that the time period after the further event exceeds the identified reference threshold value.

* * * * *

UNITED STATES PATENT AND TRADEMARK OFFICE
CERTIFICATE OF CORRECTION

PATENT NO.        : 8,471,712 B2  
APPLICATION NO. : 12/531940  
DATED             : June 25, 2013  
INVENTOR(S)      : Egan et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 948 days.

Signed and Sealed this
Eighth Day of September, 2015

Michelle K. Lee
*Director of the United States Patent and Trademark Office*